(12) United States Patent
Green

(10) Patent No.: US 7,823,221 B2
(45) Date of Patent: Nov. 2, 2010

(54) GARMENTS FOR HOLDING A POST-SURGICAL DRAIN SYSTEM

(75) Inventor: Jacqueline S. Green, Pensacola, FL (US)

(73) Assignee: DenDell, LLC, Pensacola, FL (US)

( * ) Notice: Subject to any disclaimer, the term of this patent is extended or adjusted under 35 U.S.C. 154(b) by 320 days.

(21) Appl. No.: 11/803,634

(22) Filed: May 16, 2007

(65) Prior Publication Data

US 2008/0282441 A1 Nov. 20, 2008

(51) Int. Cl.
*A41D 13/00* (2006.01)
(52) U.S. Cl. .............................................. 2/114; 2/247
(58) Field of Classification Search ...................... 2/114, 2/115, 102, 105, 106, 85, 95, 94, 80, 83, 2/247–251
See application file for complete search history.

(56) References Cited

U.S. PATENT DOCUMENTS

| | | | |
|---|---|---|---|
| 4,533,355 A | 8/1985 | Fair | |
| 4,578,062 A | 3/1986 | Schneider | |
| 4,582,508 A | 4/1986 | Pavelka | |
| 4,637,075 A * | 1/1987 | Ingrisano et al. | 2/94 |
| 4,666,432 A | 5/1987 | McNeish et al. | |
| 4,698,848 A | 10/1987 | Buckley | |
| 5,067,178 A | 11/1991 | Katchka | |
| 5,182,815 A * | 2/1993 | Young | 2/406 |
| 6,076,195 A | 6/2000 | Klein | |
| RE36,869 E | 9/2000 | Ewen | |
| 6,460,187 B1 | 10/2002 | Siegel | |
| 6,477,710 B1 * | 11/2002 | Ojoyeyi | 2/69 |
| 6,574,800 B1 | 6/2003 | Leger et al. | |
| 6,647,552 B1 * | 11/2003 | Hogan | 2/114 |
| 6,973,673 B2 | 12/2005 | Beuk | |
| 7,010,812 B1 | 3/2006 | Cho et al. | |
| 7,293,295 B2 * | 11/2007 | King | 2/114 |
| 2004/0226073 A1 | 11/2004 | McCullar et al. | |

\* cited by examiner

*Primary Examiner*—Gloria Hale
(74) *Attorney, Agent, or Firm*—Peter Loffler

(57) ABSTRACT

A garment worn by a user has an inner wearer-facing surface and an outer surface. An inner pocket is attached to the inner surface below the chest of the user, the inner pocket having a rounded bottom, an open top, and outwardly flared sides. A drain system has a drain bulb snugly received within the inner pocket and a tube with one end attached to the bulb and the opposing end indwelled within the wearer. One or more straps are located on the inner surface, the straps each forming a closed loop such that the tube passes through the loop. An outer pocket is attached to the outer surface of the garment and overlays the inner pocket so that a single stitch line attaches both the inner pocket and the outer pocket to the garment.

19 Claims, 5 Drawing Sheets

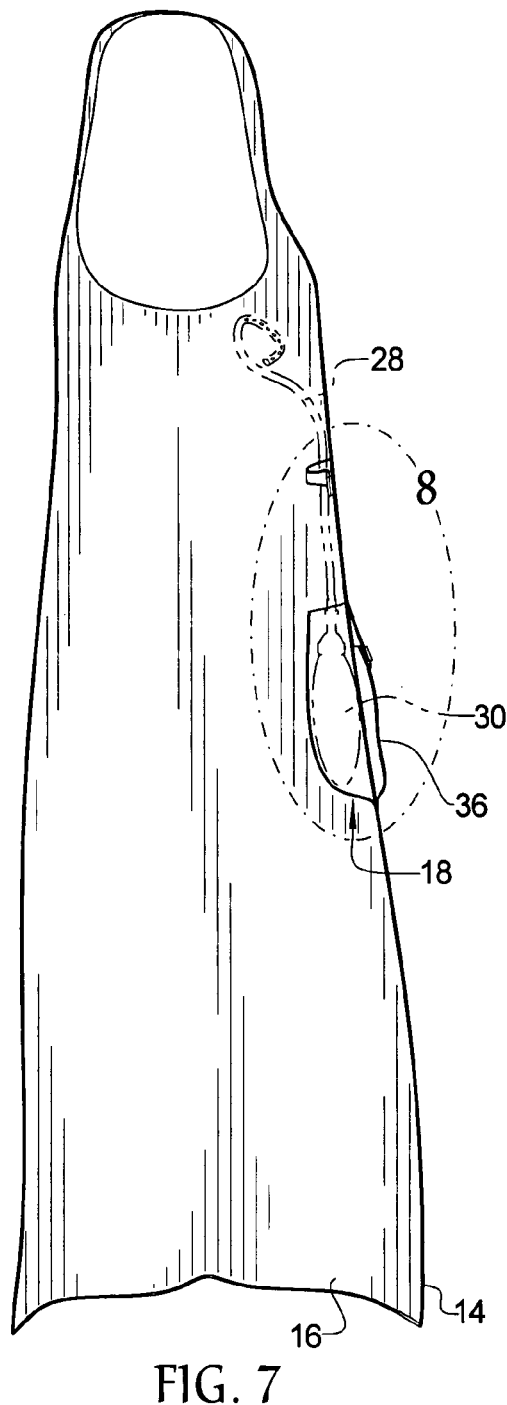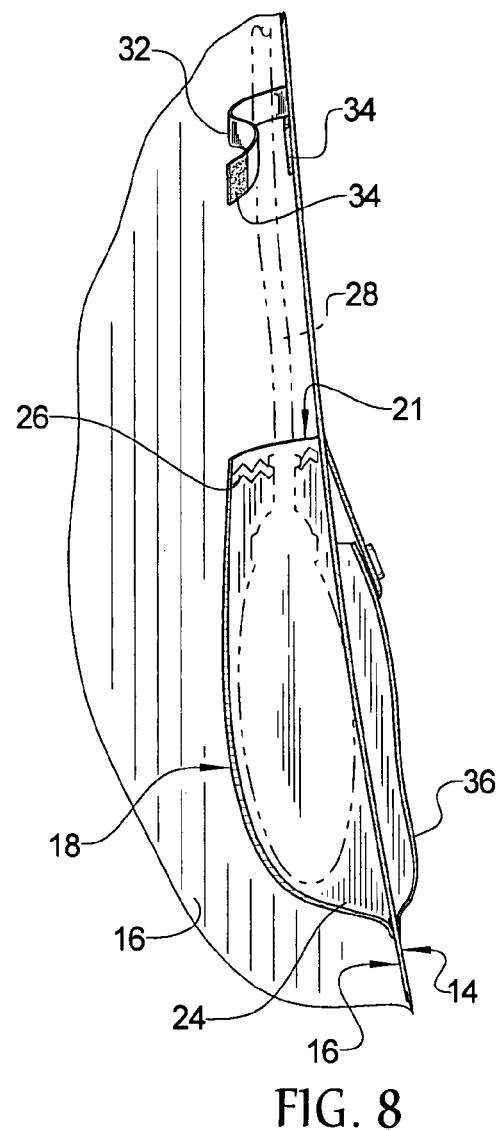
FIG. 7
FIG. 8

GARMENTS FOR HOLDING A POST-SURGICAL DRAIN SYSTEM

BACKGROUND OF THE INVENTION

1. Field of the Invention

The present invention relates to various garments that hold Jackson-Pratt type post-surgical drain bulbs and tubes so as to conceal such drainage systems from public view.

2. Background of the Prior Art

Following a surgery such as a mastectomy and the reconstructive procedures that follow the mastectomy, a patient is left with a dressing over the incision or wound where the surgery was performed. In addition, a drain tube emanates from the wound or incision site which tube terminates in a drain bulb. Such a drainage system, often referred to as a Jackson-Pratt drain, allows for removal of fluids from the surgical sight and out of the patient's body where such fluids are collected in the drain bulb and thereafter disposed.

While such post-surgical drains are necessary to prevent infections and other post-surgical complications, the drains pose certain problems for the patient. As most patients desire to become ambulatory as quickly as possible after the surgery, the drain system must be carried by the patient. While the patient is in the hospital, this typically poses few problems as many patients are carrying some form of medical appliance. However, when the patient gets back to the real world and must carry the drain system when in public, the drain system, which can be rather unsightly for non-medically trained persons, can make many patients quite self-conscious if the drain system can be viewed by others.

Some patients simply carry the drains system about without much thought or attention to what others think or say. However, many other patients attempt to hide or otherwise conceal the drain system from plain view. One of the simplest concealment methods is to simply carry the drain system, including the bulbs and associated tubing, underneath clothing and using the clothing to somehow secure the drain system. While this method works to some extent, it can be quite difficult to use a waist band or other article of clothing to securely hold the drain system so as to give the patient reasonable freedom of movement. As a result, many such patients must be careful of their every movement less they disturb the drain system or otherwise cause a painful pull on the tubing.

Other patients place the bulbs into either outer pockets or a fanny pack and conceal most of the tubing underneath the clothing having only a small portion of the tubing exposed to view. Still others place the bulbs into outer pockets and wear over-clothes so as to have a concealment layer of clothing. Although these methods generally provides a more secure method of holding the drain system, such methods still tend to be somewhat awkward for the patient and limit the selection of clothing that can be worn.

To address these concerns, specialized clothing has been proposed which clothing is designed to help a patient hold a drain system concealed from public view. Such clothing, which gives a user substantial freedom of movement, tends to be function driven so as to properly hold the drain system. As a result, fashion takes a back seat restricting the looks a patient can achieve. Other clothing, which looks more normal style-wise, tends to either be relatively complex in its holding feature, making such clothing relatively expensive to manufacture, or holds the drain system loosely so that the drain system moves about during the performance of normal activities by the user. This can result in many problems including having the drain system becoming exposed to view and causing a painful pull on the tubing at the incision site, among others. Additionally, such concealment systems tend to leave the patient with a bulge protruding through the clothing which tends to look unnatural.

Accordingly, there exists a need in the art for a device that allows a patient who has a Jackson-Pratt type drain system to be able to perform normal everyday activities in public while carrying the drain system. Such a device must conceal the drain system from public view while allowing the patient to have a broad range of movement without fear of the drain system becoming inadvertently exposed. Such a device must allow for normal clothing styles that are not unduly expensive relative to their non-drain-system holding counterparts. Such a device must minimize the risk of the drain system creating a painful pull on its tubing at the incision site and should not create an unnatural looking bugle on the clothing of the patient.

SUMMARY OF THE INVENTION

The garments for holding a post-surgical drain system of the present invention address the aforementioned needs in the art by providing normal styled garments that securely hold one or more Jackson-Pratt type of drain systems and allow the patient to perform normal everyday activities in public. The garments for holding a post-surgical drain system conceal the drain system from public view while allowing the patient to have a broad range of movement without fear of the drain system becoming inadvertently exposed. The garments for holding a post-surgical drain system can be used with many normal clothing styles and are not unduly expensive relative to their non-drain-system holding counterparts. The present invention minimizes the risk of the drain system creating a painful pull on its tubing at the incision site through the wearing of the garments and helps conceal any unnatural looking bugles that may otherwise appear on clothing being worn by the patient.

The garments for holding a post-surgical drain system of the present invention is comprised of a garment, of any appropriate style including a dress, a lounge top, a shirt, a blouse, a pair of shorts, etc., the garment to be worn by a user. The garment has an inner user-facing surface and an outer surface. An inner pocket is attached to the inner surface of the garment such that the inner pocket has a rounded bottom and an open top with a hem thereat. The hem is joined to the closed bottom by a pair of sides. A drain system has a tube with a first end that is indwelled within the patient and a second end that is attached to a collection bulb, the collection bulb being snugly located within the closed bottom of the inner pocket. Each of the pair of sides of the inner pocket flair outwardly in proceeding from the closed bottom to the hem. An elastic member is disposed within the hem. A strap has a first end that is attached to the inner surface of the garment and a second end that is removably attached to the inner surface of the garment in order to form a closed loop such that the tube passes through the loop. An outer pocket is attached to the outer surface of the garment and overlays the inner pocket. A single stitch line is used to attach both the inner pocket and the outer pocket to the garment.

BRIEF DESCRIPTION OF THE DRAWINGS

FIG. 7 is a section view of the garment of FIG. 6 taken along line 7-7 in FIG. 6.

FIG. 8 is a detail view of the loop, inner pocket and outer camouflage pocket.

Similar reference numerals refer to similar parts throughout the several views of the drawings.

DESCRIPTION OF THE PREFERRED EMBODIMENT

Figure 1:
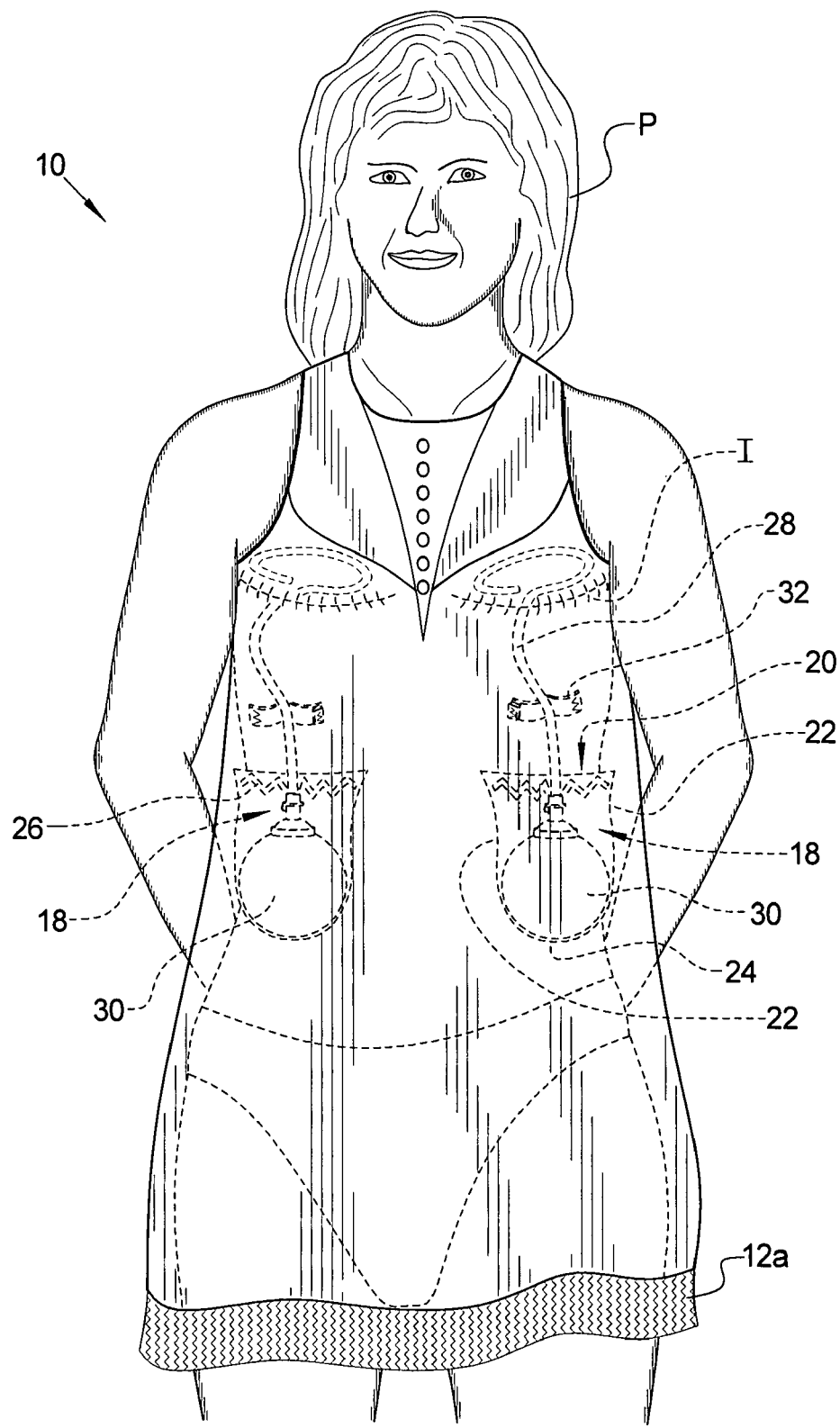
FIG. 1 is an elevation view of the garments for holding a post-surgical drain system of the present invention in the form of a sun dress holding two drain systems.

Referring now to the drawings, it is seen that the garments for holding a post-surgical drain system, generally referred to by reference numeral 10, is comprised of a typical garment such as the sun dress illustrated in FIG. 1. The garment has an outer surface 14 and an inner, user facing surface 16. Located on the inner surface 16 of the garment 12a, below the chest of the user P, is at least one inner pocket 18. Each pocket has an open top 20 defined by an upper hem 21 and a pair of sides 22 terminating at a closed bottom 24. As seen the closed bottom 24 is rounded with each side 22 of the pocket 18 flaring outwardly in proceeding toward the open top 20 so that the open top 20 is wider than the closed bottom 24. If desired, the hem 21 may have an elastic member 26 sewn therein. A drain system (which is defined as a Jackson-Pratt or a Jackson-Pratt type of system) has a drain tube 28 that has one end indwelled within the user P at the incision site I and has a collection bulb 30 located at the opposing end. The drain bulb 30 is received within one of the pockets 18 of the garment 12a. The closed bottom 24 of the pocket 18 snugly receives the drain bulb 30, which means that the closed bottom 24 of the inner pocket 18 is rounded to match the shape the lower portion of the drain bulb 30 and the inner pocket 18 is dimensioned to be substantially similar in size to the size of the drain bulb 30 so that the drain bulb 30 is received at the closed bottom 24 of the pocket 18 and held firmly thereat due to the substantially similarity of sizes between the closed bottom 24 and the drain bulb 30 without allowing lateral movement of the drain bulb 30 at the closed bottom 24 of the pocket 18.

If desired, one or more securement straps 32 can be provided such that one end of the securement strap 32 is fixedly attached to the inner surface 16 of the garment 12a and the other end of the strap 32 is removably attached to the inner surface 16 of the garment by appropriate means such as the illustrated cooperating portions of hook and loop (including the newer hook and dart) attachment system 34. The straps 32 help hold the drain tube 28 relatively steady when the user P is wearing the garment 12a and moving about.

If desired, a corresponding outer pocket 36 can be located on the outer surface 14 of the garment such that this outer pocket 36 overlays the inner pocket 18 located on the inner surface 16 of the garment. By providing an outer pocket 36 in such fashion, any bulge produced by having a drain bulb 30 within the inner pocket 18, simply appears to be an item being held within the outer pocket 36 to casual observers. The outer pocket 36 also helps conceal the stitch lines 38 used to attach the inner pocket 18 to the garment 12a as a single set of stitches 38 can be used to attach the inner pocket 18 and the outer pocket 36 to the garment 12a simultaneously.

Figure 2:
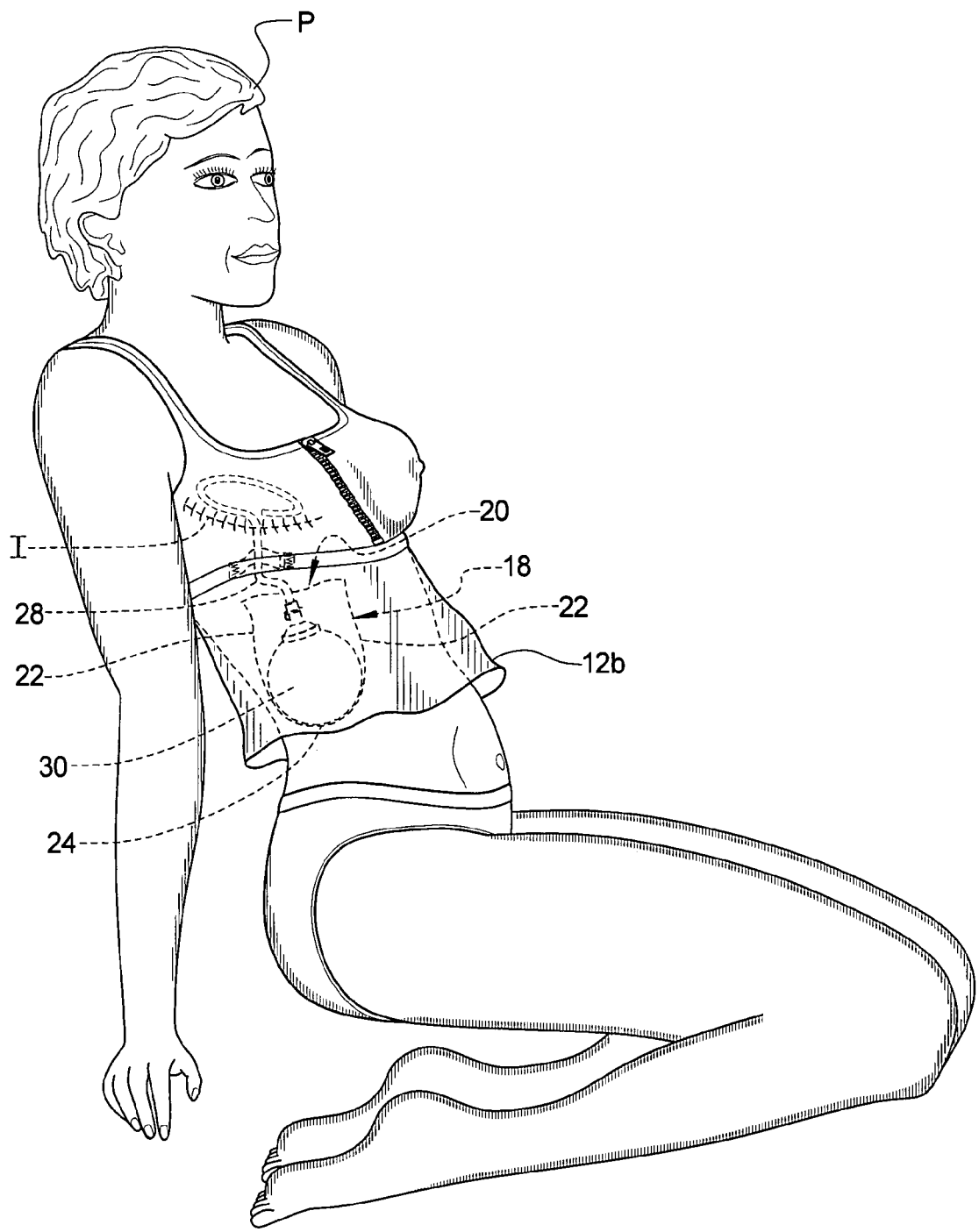
FIG. 2 is a perspective view of the garments for holding a post-surgical drain system in the form of a lounge top holding a single drain system.
Figure 3:
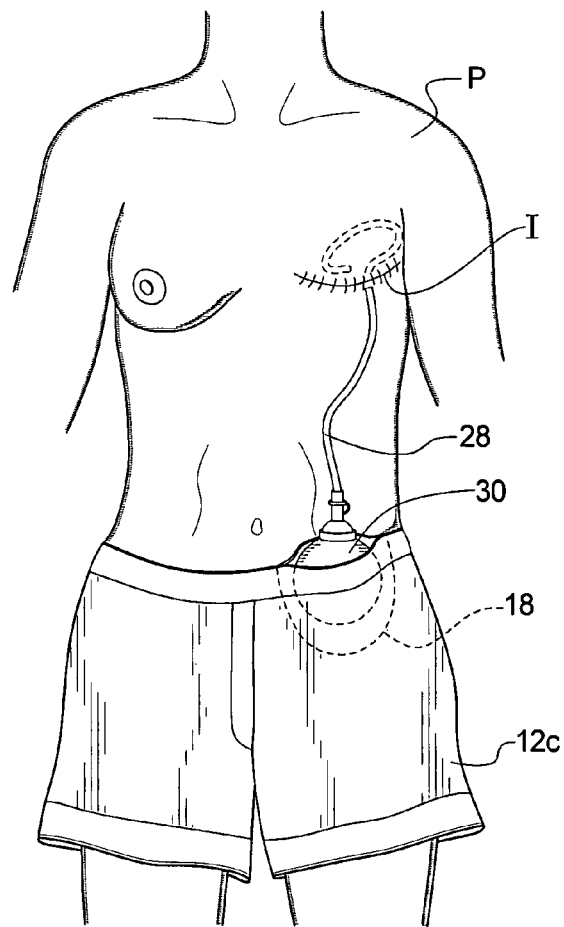
FIG. 3 is an elevation view of the garments for holding a post-surgical drain system in the form of a pair of shorts holding a single drain system.
Figure 4:
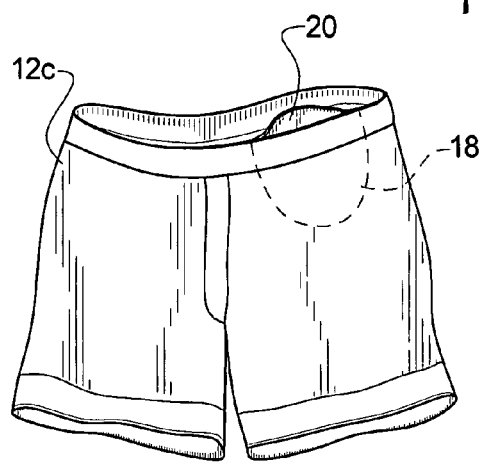
FIG. 4 is a perspective view of the shorts of FIG. 3.
Figure 5:
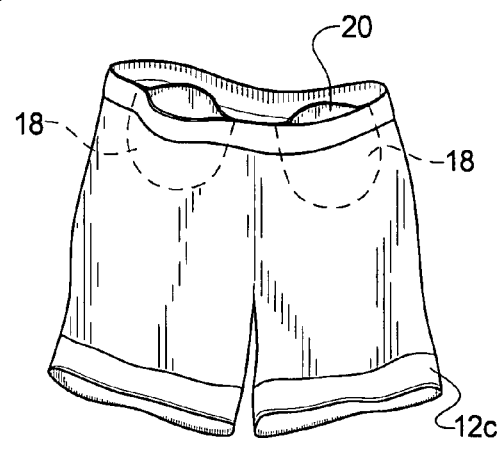
FIG. 5 is a perspective view of the garments for holding a post-surgical drain system in the form of a pair of shorts holding two drain systems.
Figure 6:
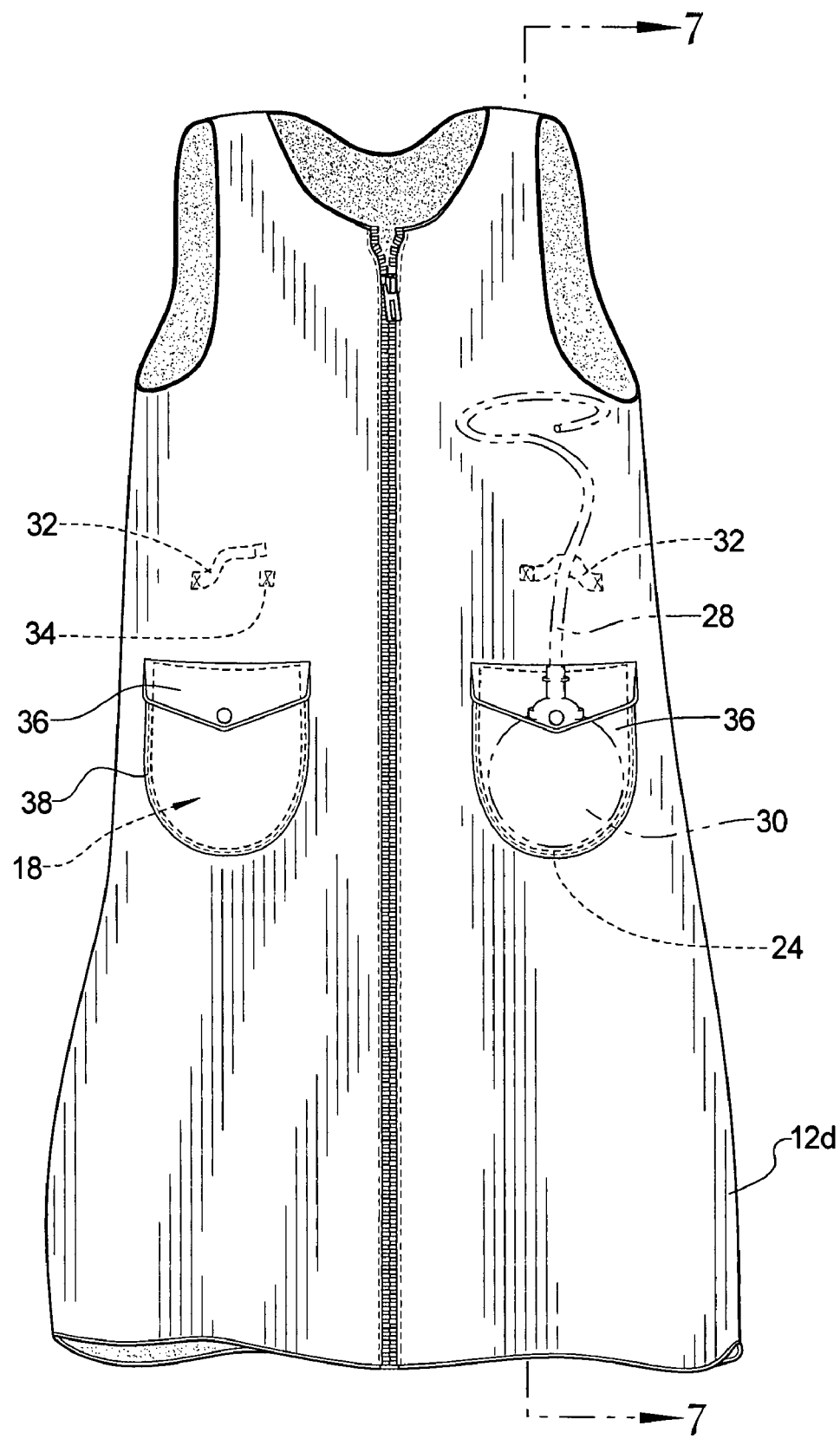
FIG. 6 is a perspective view of the garments for holding a post-surgical drain system in the form of a zipper-front dress holding two drain systems.

As seen, the garment can have many typical clothing forms including the lounge top 12b (FIG. 2), the shorts 12c (FIGS. 3-5), the zipper-front dress 12d (FIG. 6), etc. Each of the garments can be configured for holding either a single drain bulb 30 or two drain bulbs 30. If the garment is in the form of a pair of shorts 12c or other similar lower body wear, then the corresponding top (not illustrated) may come equipped with the optional straps 32 on its inner surface in order to hold the drain tube 28 as the drain tube 28 passes between the incision site I and the inner pocket 18.

In order to use the garments for holding a post-surgical drain system 10 of the present invention, the user P dawns the desired garment. Thereafter, the drain bulb 30 is placed into an inner pocket 18 and the straps 32 are opened so as to receive the drain tube 28, and thereafter the straps 32 are reattached to the inner surface 16 of the garment in order to hold the drain tube 28 securely thereat. The user P performs desired activities in the usual way. The relatively wide open top 20 of the inner pocket 18 allows the user P to be able to quickly and easily slip the drain bulb 30 into the inner pocket 18, while the snug fit of the drain bulb 30 within the closed bottom 24 of the inner pocket 18 helps hold the drain bulb 30 within the inner pocket 18 even if the user P is performing strenuous activities. The optional elastic member 26 at the hem 21 helps retain the drain bulb 30 within the inner pocket 18 if an accidental tug is exerted onto the drain tube 28. The optional straps 32 help secure the drain tube 28 and prevent excessive movement of the drain tube 28 so as to minimize the potential for a painful tug of the drain tube 28 at the incision site I. The quick disconnect and reconnect nature of the straps 32 assure speedy attachment of and removal of the drain tube 28 to the garment.

While the invention has been particularly shown and described with reference to an embodiment thereof, it will be appreciated by those skilled in the art that various changes in form and detail may be made without departing from the spirit and scope of the invention.

I claim:

1. A drain collection holding system comprising:
   a patient gown garment adapted to be worn by a user, the garment having an inner user-facing surface, and an outer surface;
   an inner pocket attached to the inner surface of the garment, the inner pocket having a closed bottom and an open top having a hem thereat, the hem joined to the closed bottom by a pair of sides;
   an outer pocket attached to the outer surface of the garment and overlaying the inner pocket; and
   a drain system having a tube with a first end adapted to be indwelled within the user and a second end attached to a collection bulb, the collection bulb located within the closed bottom of the inner pocket.

2. The holding system as in claim 1 wherein each of the pair of sides flair outwardly in proceeding from the closed bottom to the hem.

3. The holding system as in claim 2 further comprising an elastic member disposed within the hem.

4. The holding system as in claim 1 further comprising a strap having a first end attached to the inner surface of the garment and a second end removably attached to the inner surface of the garment forming a closed loop such that the tube passes through the loop.

5. The holding system as in claim 1 wherein a single stitch line is used to attach both the inner pocket and the outer pocket to the garment.

6. The holding system as in claim 1 wherein each of the pair of sides flair outwardly in proceeding from the closed bottom to the hem.

7. The holding system as in claim 6 further comprising an elastic member disposed within the hem.

8. A drain collection holding system comprising:
- a garment adapted to be worn by a user, the garment having an inner user-facing surface, and an outer surface;
- an inner pocket attached to the inner surface of the garment, the inner pocket having a closed bottom and an open top having a hem thereat, the hem joined to the closed bottom by a pair of sides;
- an outer pocket attached to the outer surface of the garment and overlaying the inner pocket; and
- a drain system having a tube with a first end adapted to be indwelled within the user and a second end attached to a collection bulb, the collection bulb being snugly located within the closed bottom of the inner pocket.

9. The holding system as in claim 8 wherein each of the pair of sides flair outwardly in proceeding from the closed bottom to the hem.

10. The holding system as in claim 9 further comprising an elastic member disposed within the hem.

11. The holding system as in claim 8 further comprising a strap having a first end attached to the inner surface of the garment and a second end removably attached to the inner surface of the garment forming a closed loop such that the tube passes through the loop.

12. The holding system as in claim 8 wherein a single stitch line is used to attach both the inner pocket and the outer pocket to the garment.

13. The holding system as in claim 8 wherein each of the pair of sides flair outwardly in proceeding from the closed bottom to the hem.

14. The holding system as in claim 13 further comprising an elastic member disposed within the hem.

15. A drain collection holding system comprising:
- a patient gown garment adapted to be worn by a user, the garment having an inner user-facing surface, and an outer surface;
- an inner pocket attached to the inner surface of the garment, the inner pocket having a closed bottom and an open top having a hem thereat, the hem joined to the closed bottom by a pair of sides;
- a strap having a first end attached to the inner surface of the garment and a second end removably attached to the inner surface of the garment, the strap and the inner surface of the garment forming a closed loop, the strap being located in spaced apart relationship with and above the pocket;
- an outer pocket attached to the outer surface of the garment and overlaying the inner pocket; and
- a drain system having a tube with a first end adapted to be indwelled within the user and a second end attached to a collection bulb, the collection bulb located within the closed bottom of the inner pocket such that the tube passes through the loop.

16. The holding system as in claim 15 wherein each of the pair of sides flair outwardly in proceeding from the closed bottom to the hem.

17. The holding system as in claim 16 further comprising an elastic member disposed within the hem.

18. The holding system as in claim 15 wherein a single stitch line is used to attach both the inner pocket and the outer pocket to the garment.

19. The holding system as in claim 15 wherein each of the pair of sides flair outwardly in proceeding from the closed bottom to the hem.

* * * * *